(12) United States Patent
Klinnert (10) Patent No.: US 8,771,073 B2
(45) Date of Patent: Jul. 8, 2014

(54) INTERACTIVE SPORTING APPARATUS

(75) Inventor: Ralf Klinnert, Edinburgh (GB)

(73) Assignee: Funky Moves Ltd, Livingston (GB)

( * ) Notice: Subject to any disclaimer, the term of this patent is extended or adjusted under 35 U.S.C. 154(b) by 1004 days.

(21) Appl. No.: 13/060,145

(22) PCT Filed: Aug. 22, 2008

(86) PCT No.: PCT/GB2008/050736
§ 371 (c)(1),
(2), (4) Date: Feb. 22, 2011

(87) PCT Pub. No.: WO2009/024827
PCT Pub. Date: Feb. 26, 2009

(65) Prior Publication Data
US 2011/0148039 A1    Jun. 23, 2011

(30) Foreign Application Priority Data

Aug. 23, 2007   (GB) .................................. 0716459.3

(51) Int. Cl.
*A63F 9/24*       (2006.01)
*A63F 13/00*      (2006.01)
*G06F 17/00*      (2006.01)
*G06F 19/00*      (2011.01)

(52) U.S. Cl.
USPC .................... 463/36; 463/39; 463/40; 463/41; 463/42; 463/43

(58) Field of Classification Search
USPC ............................... 463/36, 39, 40, 41, 42, 43
See application file for complete search history.

(56) References Cited

U.S. PATENT DOCUMENTS

| 4,627,620 A | 12/1986 | Yang |
| 4,645,458 A | 2/1987 | Williams |
| 4,919,418 A | 4/1990 | Miller |
| 2003/0045203 A1 | 3/2003 | Sabe et al. |
| 2004/0266563 A1* | 12/2004 | Young .......................... 473/446 |
| 2006/0179303 A1* | 8/2006 | Gurleyen et al. ............. 713/167 |

(Continued)

FOREIGN PATENT DOCUMENTS

| CA | 2169969 | 2/1998 |
| FR | 2 700 346 | 7/1994 |

(Continued)

OTHER PUBLICATIONS

Office Action (2 pgs.) dated May 18, 2012 issued in corresponding GB Application No. 1104823.8.

(Continued)

*Primary Examiner* — Adetokunbo O Torimiro
(74) *Attorney, Agent, or Firm* — Nixon & Vanderhye PC (57) ABSTRACT

There is disclosed interactive sporting apparatus comprising a control unit (2) and a plurality of interactive units (4), the interactive units comprising: at least one signalling device (52,54) which is operable to generate a sensory stimulus or a signalling device interface adapted (51) to demountably retain a signalling device for generating a sensory stimulus; and at least one sensor (54) which is operable by a game participant proximate to an interactive unit to generate a sensing event or a sensor interface adapted to demountably retain a sensor operable by a game participant proximate to an interactive unit to generate a sensing event; wherein the control unit is operable to communicate remotely with the plurality of interactive units to specify sensory stimuli to be generated by the plurality of interactive units.

26 Claims, 3 Drawing Sheets

(56) References Cited

U.S. PATENT DOCUMENTS

| | | |
|---|---|---|
| 2006/0205569 A1 | 9/2006 | Watterson et al. |
| 2007/0179412 A1 | 8/2007 | Imboden et al. |
| 2008/0051228 A1 | 2/2008 | Harmon et al. |

FOREIGN PATENT DOCUMENTS

| | | |
|---|---|---|
| FR | 2 713 944 | 6/1995 |
| GB | 2179777 | 3/1987 |
| GB | 2232898 | 1/1991 |
| GB | 2332630 | 6/1999 |
| GB | 2 389 743 | 12/2003 |
| GB | 2 407 941 | 6/2005 |
| JP | 64-18242 | 1/1989 |
| JP | 2001-123419 | 5/2001 |
| WO | 90/11108 | 10/1990 |
| WO | 01/00281 | 1/2001 |
| WO | WO 01/00281 | 1/2001 |
| WO | 02/067449 | 8/2002 |
| WO | WO 02/067449 | 8/2002 |
| WO | 2005/107890 | 11/2005 |
| WO | WO 2005/107890 | 11/2005 |
| WO | 2006/099320 | 9/2006 |
| WO | 2007/009072 | 1/2007 |
| WO | WO 2007/009072 | 1/2007 |
| WO | 2007/142588 | 12/2007 |

OTHER PUBLICATIONS

Office Action (2 pgs.) dated Jan. 17, 2013 issued in corresponding GB Application No. 1104823.8.
International Search Report for PCT/GB2008/050736, mailed Dec. 22, 2008.
Written Opinion of the International Searching Authority for PCT/GB2008/050736, mailed Dec. 22, 2008.

* cited by examiner

INTERACTIVE SPORTING APPARATUS

This application is the U.S. national phase of International Application No. PCT/GB2008/050736 filed 22 Aug. 2008, the entire contents of which is hereby incorporated by reference.

FIELD OF THE INVENTION

The present invention relates to electronic sporting apparatus, particularly interactive electronic sporting apparatus.

BACKGROUND TO THE INVENTION

A variety of electronic sporting apparatus have been proposed for conducting sporting games designed to train the physical and/or mental abilities of one or more participants.

For example, it is known to provide apparatus which generate sensory stimuli which dictate activities to be carried out by participants in a sporting game. It has also been proposed to provide more interactive apparatus, such as apparatus which includes a base station attached by a wired connection to stations which include a light and a switch. When the switch attached to a particular station is pressed, the base station causes the light attached to another identical station to light up. This apparatus has only a limited number of practical sporting applications and can generally only be used by a single participant at a time.

The present invention aims to provide improved sporting apparatus which is interactive and can be used to conveniently implement and manage a range of sporting games.

Some aspects of the invention are directed to sporting apparatus which is usable by a plurality of participants at the same time and which, in some circumstances, is operable to record performance data relating to individual participants who use the apparatus simultaneously.

Further benefits will be apparent from the following description.

SUMMARY OF THE INVENTION

According to the present invention, there is provided interactive sporting apparatus comprising a control unit and a plurality of interactive units, the interactive units comprising:
  at least one signalling device which is operable to generate a sensory stimulus or a signalling device interface adapted to demountably retain a signalling device for generating a sensory stimulus; and
  at least one sensor which is operable by a game participant proximate to an interactive unit to generate a sensing event or a sensor interface adapted to demountably retain a sensor operable by a game participant proximate to an interactive unit to generate a sensing event;
  wherein the control unit is operable to communicate remotely with the plurality of interactive units to specify sensory stimuli to be generated by the plurality of interactive units.

The signalling devices may be integral to each interactive unit. Alternatively, in embodiments which employ a signalling device interface, a signalling device selected from a group of different signalling devices can be demountably retained by the signalling device interface of a particular interactive unit allowing for individual customisation of each interactive unit.

The sensors may be integral to each interactive unit. Alternatively, in embodiments which employ a sensor interface, a sensor selected from a group of different sensors can be demountably retained by the sensor interface of a particular interactive unit allowing for individual customisation of each interactive unit.

Preferably, the interactive sporting apparatus is operable to record data relating to sensing events. For example, the interactive sporting apparatus may be operable to record the period of time which elapses between a sensory stimulus generated by a signalling device and a sensing event, or the period of time between sensing events generated on two separate interactive units.

Data relating to sensing events may be recorded by the plurality of interactive units and relayed to the control unit. Data relating to sensing events (for example, data communicating that a sensing event has taken place) may be relayed from an interactive unit to the control unit and stored by the control unit. The control unit may be operable to calculate data concerning sensing events which took place at a plurality of different interactive units, for example, the period of time between a sensing event at a first interactive unit and a subsequent sensing event at a second interactive unit.

The control unit and the plurality of interactive units may communicate using wired connections. However, the control unit and the plurality of interactive units are preferably adapted to communicate wirelessly. Each interactive unit may be adapted to communicate directly with the control unit. Alternatively, or as well, each interactive unit may be adapted to communicate with other interactive units.

Accordingly, the control unit and the plurality of interactive units may be operable to form a wireless communications network. To facilitate wireless communication, the control unit and each interactive unit may comprise a wireless transceiver, for example a radio-frequency wireless transceiver. Alternatively, or additionally, the control unit and the plurality of interactive units may be operable to communicate ultrasonically or by using infra-red light.

Preferably, each interactive unit comprises a programmable electronic processor, such as a microprocessor or microcontroller, which is operable to control the generation of sensory stimuli by the signalling device dependent on a program. The electronic processor may also be responsive to a sensing event generated by a sensor. A received program may determine actions carried out in response to a sensing event or may specify performance data which is recorded, where relevant. The interactive units may be operable to generate sensory stimuli responsive to sensing events, as specified by a program. A program may comprise either or both program code which determines actions to be carried out by the electronic processor and data which defines actions, such as sound data which specifies an audible sensory stimulus.

The control unit may be operable to distribute different programs to different interactive units. The control unit may be operable to distribute the same program to different interactive units, but different interactive units may be adapted to respond differently to the program, for example, they may respond to different parts of the same program or the program may comprise data which relates to different interactive units. Accordingly, interactive sporting apparatus may be provided in which two or more of the plurality of interactive units interact differently, for example, two or more of the plurality of interactive units may generate different sensory stimuli (e.g. different sounds, such as different spoken commands) responsive to sensing events.

Alternatively, or as well, the control unit may comprise a programmable electronic processor, such as a microprocessor or microcontroller, which is operable to control the generation of sensory stimuli by the interactive units responsive to a program executed by the control unit. The control unit may be operable to transmit instructions to interactive units to generate sensory stimuli responsive to receiving data from an interactive unit which indicates that a sensing event has occurred.

The interactive units may generate a sensory stimulus responsive to a sensing event occurring at the same interactive unit. For example, a sensory stimulus may be generated by the signalling device of an interactive unit responsive to a sensing event at the same interactive unit. This response may be determined without reference to the control unit or other interactive units, under the control of the individual interactive unit.

The interactive units may generate a sensory stimulus responsive to a sensing event occurring at a different interactive unit. For example, a sensory stimulus may be generated responsive to a sensing event at a different interactive unit. To facilitate this, a first interactive unit may transmit a message to a second interactive unit responsive to a sensing event at the first interactive, or a first interactive unit may transmit a message to the control unit responsive to a sensing event whereupon the control unit transmits a message to the second interactive unit. The sensory stimulus generated by the second interactive unit may be determined by a program prestored at the second interactive unit or may be determined by data sent to the second interactive unit by the control unit.

The signalling device may be operable to generate a visual stimulus. For example, the signalling device may comprise a light. The signalling device may be operable to generate an audio stimulus, such as a sound. The signalling device may be operable to generate speech, such as a spoken command or instruction. Apparatus may be provided in which two or more of the interactive units are operable to generate different stimuli. Two of more of the interactive units may be operable to generate different stimuli in response to equivalent sensing events, for example to generate different sounds, such as different spoken commands or instructions, responsive to the pushing of a button on the interactive unit.

The interactive units may be operable to generate sensory stimuli at specific times, for example specific times after a program is started. A program may be started by an instruction generated by the control unit responsive to an input from a user of the control unit (the controller).

The control unit may comprise input devices, such as buttons on a keyboard, switches or regions on a touch screen, corresponding to particular interactive units, which is operable to cause a corresponding interactive unit to generate a sensory stimulus responsive to operation of the input devices by the controller.

Alternatively, a personal computer, such as a laptop computer or a personal digital assistant (PDA), may function as the control unit directly. In this case, the plurality of interactive units communicates directly with the personal computer. A program may be started by an instruction generated by the personal computer, functioning as the control unit, responsive to an input from a user of the personal computer.

Alternatively, the control unit may be adapted to communicate with and receive instructions from an external computer. In this case, the control unit preferably comprises an external electronic interface which is operable to communicate with an external user interface, such as an external computer, such that the external user interface is in electronic communication with the control unit. The external electronic interface may be a wireless interface to facilitate wireless communication. Equally, the external electronic interface may be a wired interface.

The control unit may be operable to communicate stored performance data to the external computer.

The sensor may comprise a manually operated button or switch. The button or switch may be located on the top of the interactive device. The button or switch may be located towards the base of the interactive device. The button or switch may be operable by the wheel of a wheelchair. The sensor may require physical contact by a game participant in order to generate a sensing event. The sensor may be operable by a projectile, such as a bean bag, thrown by a game participant in order to generate a sensing event.

The sensor may be remotely actuated. In this case, the sensor may comprise a light barrier operable between two or more interactive units. The light barrier may be actuated by a game participant or a projectile breaking the light barrier between the two or more interactive units. In this case, a first interactive unit emits a beam of light (such as infra-red light) and a second interactive unit receives the beam of light and detects when it is broken. Alternatively, or additionally, the sensor may comprise a proximity sensor operable by a game participant or a projectile proximate to the sensor.

The control unit may be operable to record performance data relating to one or more participants in a sporting game. The performance data may relate to the period of time between a sensory stimulus and a sensing event. The performance data may relate to the period of time between two sensing events. The performance data may relate to the period of time between the start and end of a series of sensing events, such as sensing events in which a participant in a sporting game operates a sensor on a plurality of the interactive units, perhaps in a defined sequence.

The control unit may be operable to record performance data relating to two or more participants or groups of participants who take part in a sporting game using the interactive sporting apparatus simultaneously or consecutively. For example, it may allocate the time between some sensory stimuli and sensing events to one participant of several participants who interact with the apparatus consecutively or simultaneously, and the time between other sensory stimuli and sensing events to another participant of several participants who interact with the apparatus consecutively or simultaneously.

Typically, the interactive units comprise internal power supplies so that they do not need to be permanently connected to a power source by a wired connection. Preferably, the interactive units include an interface for connection to an external power supply to charge the interactive unit, for example a mains electricity connection. The interactive units may include connectable electric contacts enabling interactive units to transfer power to adjacent interactive units, so that only some interactive units, or a single interactive unit, need to be wired into a power supply, such as a mains electricity supply, to enable the internal power supplies of the interactive units to be charged. The interactive units may be stackable and configured so that connectable electric contacts of stacked interactive units contact connectable electronic contacts of adjacent interactive units in a stack to enable power to be transferred between interactive units in a stack to charge their respective internal power supplies. The interactive units may be in the form of stackable cones.

Two or more of the interactive units may be labeled differently. For example, two or more of the interactive units may have different colours. All of the interactive units may be differently labeled, for example, all of the interactive units may have different colours. This facilitates games in which a participant is directed to go to an interactive unit, or a series of interactive units in turn, by reference to the label and/or colour of the or each interactive unit, and optionally generate one or more sensing events by operating the sensor of one or more interactive units.

The interactive sporting apparatus may be operable to generate a sequence of sensory stimuli which dictate a series of interactive units with which a participant is to interact, by reference to a label and/or colour of the series of interactive units. The interactive sporting apparatus may be operable to generate a sequence of sensory stimuli which specify a series of interactive units with which a participant is to interact, by causing the signalling devices of the interactive units with which a participant is to interact to generate a sensory stimulus in an order which corresponds to the orders in which a participant is to travel between the interactive units and operate the sensors of the interactive units. This provides a memory game. The period of time required by one or more users to travel between the specified interactive units may be recorded.

The interactive sporting apparatus may comprise identification apparatus for identifying individual game participants. Preferably, the identification apparatus comprises a plurality of unique identifying tags which may be carried by individual game participants to allow unique identification to take place and a unique identifying tag reader which is operable to read and uniquely identify a unique identifying tag. Preferably, the unique identifying tag reader may be operable to communicate data relating to unique identification to the control unit. By unique we refer to unique at least within the particular interactive sporting apparatus.

Typically, a game participant may be issued with a unique identifying tag, such as a token comprising a radio-frequency identification (RFID) tag, which is remotely readable by the unique identifying tag reader to uniquely identify the game participant. Alternatively, the unique identifying tag may require contact between said tag and the unique identifying tag reader to allow unique identification to take place. For example, the identification tag may be a swipe card or a key and the unique identifying tag reader may be a swipe card reader or key reader respectively.

Accordingly, the interactive sporting apparatus may comprise a control unit which comprises a unique identifying tag reader. Alternatively, the interactive sporting apparatus may comprise at least one interactive unit comprising a unique identifying tag reader. Alternatively, the interactive sporting apparatus comprises an identifying unit which functions to read and uniquely identify unique identifying tags, the identifying unit comprising a unique identifying tag reader. Preferably, the identifying unit is operable to communicate data relating to unique identification to the control unit.

According to a second aspect of the present invention, there is provided interactive sporting apparatus comprising a control unit and a plurality of remote units, the remote units comprising a ground engaging base having either:
(i) an interface for demountably retaining a signalling device for generating a sensory stimulus or a sensor operable by a game participant proximate to the remote unit, for generating a sensing event, or
(ii) an interface for demountably retaining a device which comprises both a signalling device for generating a sensory stimulus and a sensor operable by a game participant proximate to the remote unit, for generating a sensing event,
wherein the control unit is operable to communicate remotely with the plurality of remote units to specify sensory stimuli to be generated by one or more remote units.

In case (i), the interface of a remote unit may be adapted to demountably retain a signalling device or a sensor but not a device which comprises both a signalling device and a sensor. Alternatively, in some embodiments, the interface of a remote unit may be adapted to demountably retain a signalling device or a sensor or a device which comprises both a signalling device and a sensor.

Alternatively, in case (ii) the interface may be adapted to demountably retain a signalling device or a sensor or a device which comprises both a signalling device and a sensor. However, in case (ii), the interface may be adapted to demountably retain a device which comprises both a signalling device and a sensor but not a signalling device or a sensor.

Preferably, the control unit is operable to communicate remotely with the plurality of remote units to receive data concerning sensing events.

Preferably, the interactive sporting apparatus further comprises a plurality of exchangeable signalling devices comprising signalling devices of different types, such as lights, loudspeakers or other suitable signalling devices, which are demountably attachable to the interface of a remote unit. Further optional features of the signalling devices correspond to those discussed in relation to the first aspect above.

Preferably, the interactive sporting apparatus further comprises a plurality of exchangeable sensors comprising sensors of different types, such as manually operable sensors or remotely operable sensors, which are demountably attachable to the interface of a remote unit. Further optional features of the sensors correspond to those discussed in relation to the first aspect above.

In embodiments which employ at least one remote unit comprising an interface adapted to demountably retain a device which comprises both a signalling device and a sensor (whether or not the interface is adapted to alternatively demountably retain either a signalling device or a sensor), the sporting apparatus preferably comprises at least one device which comprises both a signalling device and a sensor which is demountably attachable to the interface of said remote units. More preferably, the sporting apparatus comprises a plurality of different exchangeable devices comprising both a signalling device and a sensor, for example a first exchangeable device may comprise a light as a signalling device and a manually operated button as a sensor and a second exchangeable device may comprise a loudspeaker as a signalling device and a proximity sensor as a sensor.

Preferably, the interactive sporting apparatus is operable to record data relating to sensing events. For example, the sporting apparatus may be operable to record the period of time which elapses between a sensory stimulus generated by a signalling device and a sensing event, or the period of time between sensing events generated on two separate remote units.

Data relating to sensing events may be recorded by a plurality of remote units and relayed to the control unit. Data relating to sensing events (for example, data communicating that a sensing event has taken place) may be relayed from a remote unit to the control unit and stored by the control unit. The control unit may be operable to calculate data concerning sensing events which took place at a plurality of different remote units, for example, the period of time between a sensing event at a first remote unit and a subsequent sensing event at a second remote unit.

The control unit and the plurality of remote units may communicate using wired connections. However, the control unit and the plurality of remote units are preferably adapted to communicate wirelessly. Each remote unit may be adapted to communicate directly with the control unit. Alternatively, or as well, each remote unit may be adapted to communicate with other remote units.

Accordingly, the control unit and the plurality of remote units may be operable to form a wireless communications network. To facilitate wireless communication, the control unit and each remote unit may comprise a wireless transceiver, for example a radio-frequency wireless transceiver. Alternatively, or additionally, the control unit and the plurality of interactive units may be operable to communicate ultrasonically or by using infra-red light.

Preferably, each remote unit comprises a programmable electronic processor, such as a microprocessor or microcontroller, which is operable to control the generation of sensory stimuli by a signalling device, where attached, dependent on a program. The electronic processor may also be responsive to a sensing event generated by a sensor, where attached. A received program may determine actions carried out in response to a sensing event or may specify performance data which is recorded, where relevant. The remote units may be operable to generate sensory stimuli responsive to sensing events, as specified by a program. A program may comprise either or both program code which determines actions to be carried out by the electronic processor and data which defines actions, such as sound data which specifies an audible sensory stimulus.

The control unit may be operable to distribute different programs to different remote units. The control unit may be operable to distribute the same program to different remote units, but different remote units may be adapted to respond differently to the program, for example, they may respond to different parts of the same program or the program may comprise data which relates to different remote units. Accordingly, interactive sporting apparatus may be provided in which two or more of the plurality of remote units generate different sensory stimuli (e.g. different sounds, such as different spoken commands) responsive to sensing events.

Alternatively, or as well, the control unit may comprise a programmable electronic processor, such as a microprocessor or microcontroller, which is operable to control the generation of sensory stimuli by the remote units responsive to a program executed by the control unit. The control unit may be operable to transmit instructions to remote units to generate sensory stimuli responsive to receiving data from a remote unit which indicates that a sensing event has occurred.

Preferably, the remote units generate a sensory stimulus responsive to a sensing event occurring at a different remote unit. To facilitate this, a first remote unit may transmit a message to a second remote unit responsive to a sensing event at the first remote unit, or a first remote unit may transmit a message to the control unit responsive to a sensing event whereupon the control unit transmits a message to the second remote unit. The sensory stimulus generated by the second remote unit may be determined by a program pre-stored at the second remote unit or may be determined by data sent to the second remote unit by the control unit.

One or more remote units may be operable to generate sensory stimuli at specific times, for example specific times after a program is started. A program may be started by an instruction generated by the control unit responsive to an input from a user of the control unit (the controller).

The control unit may comprise input devices, such as buttons on a keyboard, switches or regions on a touch screen, corresponding to particular remote units, which is operable to cause a corresponding remote unit to generate a sensory stimulus responsive to operation of the input devices by the controller.

Alternatively, a personal computer, such as a laptop computer or a personal digital assistant (PDA), may function as the control unit directly. In this case, the plurality of remote units communicates directly with the personal computer. A program may be started by an instruction generated by the personal computer, functioning as the control unit, responsive to an input from a user of the personal computer.

Alternatively, the control unit may be adapted to communicate with and receive instructions from an external computer. In this case, the control unit preferably comprises an external electronic interface which is operable to communicate with an external user interface, such as an external computer, such that the external user interface is in electronic communication with the control unit. The external electronic interface may be a wireless interface to facilitate wireless communication. Equally, the external electronic interface may be a wired interface.

The control unit may be operable to communicate stored performance data to the external computer.

A light barrier may be formed using a light generating member which is attachable to the interface of a first remote unit, for generating a beam of light (e.g. infra red light) and a light sensing member may be attachable to the interface of a second remote unit, for sensing the beam of light and detecting when the beam of light is broken, generating a sensing event.

The control unit may be operable to record performance data relating to one or more participants in a sporting game. The performance data may correspond to the performance data discussed in relation to the first aspect of the invention.

Typically, the remote units comprise internal power supplies so that they do not need to be permanently connected to a power source by a wired connection. Preferably, the remote units include an interface for connection to an external power supply to charge the remote unit, for example a mains electricity connection. The remote units may include connectable electric contacts enabling remote units to transfer power to adjacent remote units, so that only some remote units, or a single remote unit, need to be wired into a power supply, such as a mains electricity supply, to enable the internal power supplies of the remote units to be charged. The remote units may be stackable and configured so that connectable electric contacts of stacked remote units contact connectable electronic contacts of adjacent remote units in a stack to enable power to be transferred between remote units in a stack to charge their respective internal power supplies.

Two or more of the remote units, signaling devices or sensors may be labeled differently. For example, two or more of the remote units, signaling devices or sensors, may have different colours. All of the signaling devices, remote units or sensors may be differently labeled, for example, all of the signaling devices, remote units may or sensors have different colours. This facilitates games in which a participant is directed to go to a remote unit, or a series of remote units in turn, by reference to the label and/or colour of the or each remote unit, or a signaling device or sensing device attached thereto, and optionally generate one or more sensing events by operating the sensor of one or more remote units.

The interactive sporting apparatus may be operable to generate a sequence of sensory stimuli which dictate a series of remote units with which a participant is to interact, by reference to a label and/or colour of the series of remote units, or sensors attached thereto.

The interactive sporting apparatus may comprise identification apparatus for identifying individual game participants. Preferably, the identification apparatus comprises a plurality of unique identifying tags which may be carried by individual game participants to allow unique identification to take place and a unique identifying tag reader which is operable to read and uniquely identify a unique identifying tag. Preferably, the unique identifying tag reader may be operable to communicate data relating to unique identification to the control unit. By unique we refer to unique at least within the particular sporting apparatus.

Typically, a game participant may be issued with a unique identifying tag, such as a token comprising a radio-frequency identification (RFID) tag, which is remotely readable by the unique identifying tag reader to uniquely identify the game participant. Alternatively, the unique identifying tag may require contact between said tag and the unique identifying tag reader to allow unique identification to take place. For example, the identification tag may be a swipe card or a key and the unique identifying tag reader may be a swipe card reader or a key reader respectively.

Accordingly, the interactive sporting apparatus may comprise a control unit which comprises a unique identifying tag reader. Alternatively, the interactive sporting apparatus may comprise at least one remote unit comprising a unique identifying tag reader. Alternatively, the interactive sporting apparatus comprises an identifying unit which functions to read and uniquely identify unique identifying tags, the identifying unit comprising a unique identifying tag reader. Preferably, the identifying unit is operable to communicate data relating to unique identification to the control unit.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
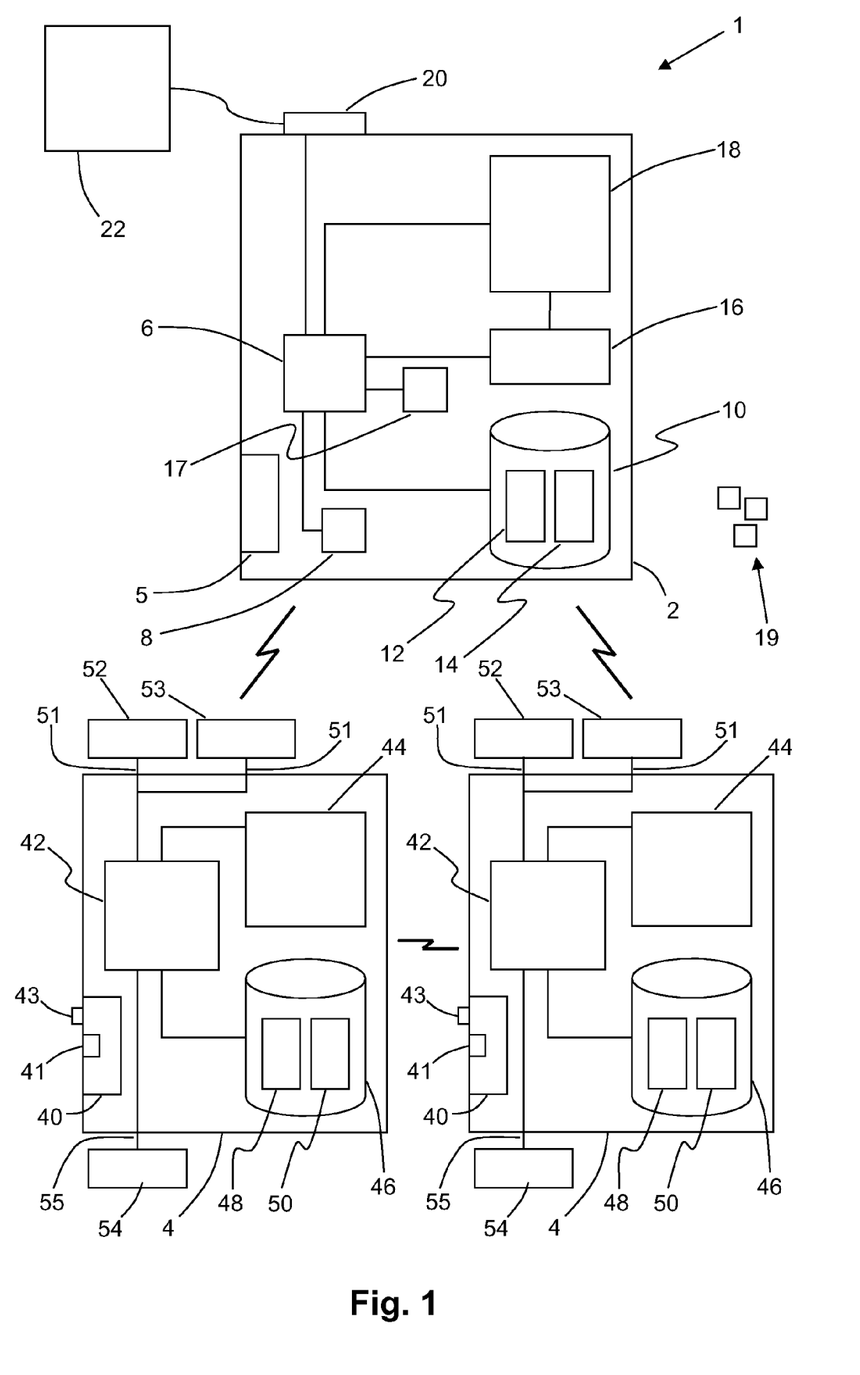
FIG. 1 is a schematic diagram of the interactive sporting apparatus.

FIG. 1 is a schematic diagram of functional components of sporting apparatus 1 which comprises a control unit 2 and a plurality of interactive units 4. The sporting apparatus further comprises a plurality of radio-frequency identifying (RFID) tags 19.

The control unit includes a power source in the form of a rechargeable battery 5, a programmable electronic microprocessor 6, a wireless transceiver 8 which is electronically connected to the microprocessor and a memory device 10 which is electronically connected to the microprocessor. The memory device stores program code 12 which is executed by the microprocessor as well as any additional relevant data 14. The control unit further comprises an RFID tag reader 17 which is electronically connected to the microprocessor and is operable to read identifying information from RFID tags in use.

The control unit comprises user interface elements including one or more input devices 16, such as a keyboard, and one or more output devices 18, such as a display, which are electronically connected to the microcontroller. A single user interface element may function as both an input device and an output device. For example, a touch screen display may constitute both an input device and an output device.

The control unit includes an external electronic interface 20. The interface is electronically connected (here by a wired connection but this could equally be a wireless connection) to an external user interface 22, for example a laptop computer. The external user interface is used to communicate the program code 12 to the control unit and to transmit performance data 14 to the external user interface. The external user interface may then be detached. Alternatively, the external user interface may remain connected to the control unit to remain in electronic communication with the control unit for the duration, or a portion of the duration, of a game.

The plurality of interactive units each include an internal power source 40, a programmable electronic microcontroller 42, a wireless transceiver 44 which is electronically connected to the microcontroller and a memory device 46 which is electronically connected to, or alternatively part of, the microcontroller. The memory device stores program code 48 which determines the actions of the relevant microcontroller as well as any additional data 50 which is required. The program code and data together function as a program.

The interactive units include wires 51, functioning as signalling device interfaces, and a wire 55, functioning as a sensor interface.

The interactive units include a loudspeaker 52 for outputting sound and a light 53 for providing a visual stimulus. The loudspeaker and light function as signalling devices which provide sensory stimuli under the control of the microcontroller, according to stored program. The interactive units include a button 54, which functions as a sensor, which is electronically connected to the microcontroller so that the microcontroller can determine when the button is pressed (which action constitutes a sensing event). The electronic components within the plurality of interactive units are situated on printed circuit boards and are mounted inside the interactive units.

Figure 2:
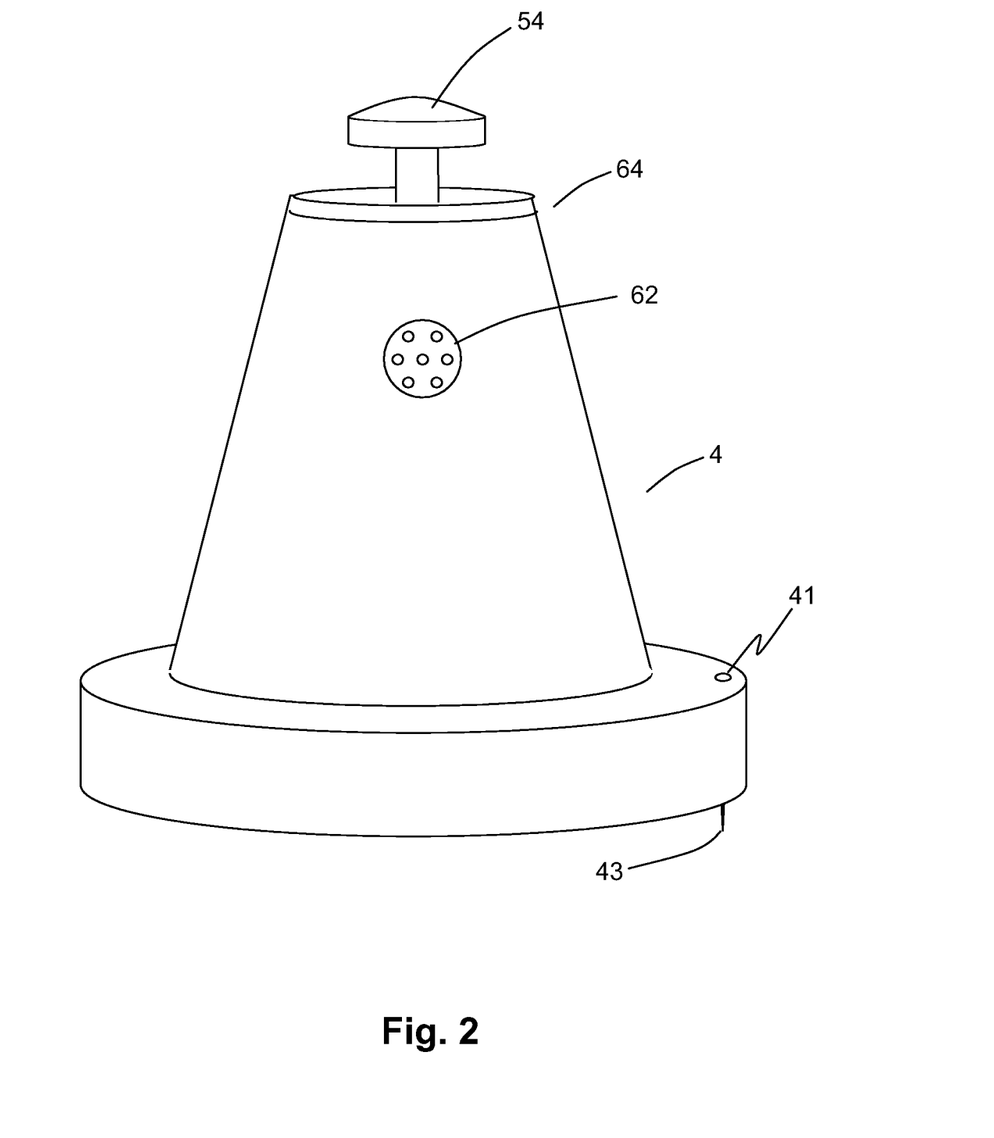
FIG. 2 is a perspective view of a preferred embodiment of one of the interactive units.

The plurality of interactive units are typically, but not exclusively, cone shaped. The plurality of interactive units typically, but not exclusively, comprise a hollow portion. FIG. 2 shows the preferred embodiment of the interactive units. In this case, the loudspeaker grill 62 and light cover 64 are located at suitable positions on the interactive unit. The interactive units are made from a lightweight material such as, but not exclusively, a plastics material. The interactive units are different colours so that they can be distinguished from each other.

When not in use the internal power source of the control unit can be recharged by electrical connection to an external power source such as mains electricity. The interactive units include electronic contacts comprising a socket 41 and a plug 43 which are arranged, so that when the interactive units are stacked upon each other, the electronic contacts of successive units within the stack are operable to transfer electric current to a neighbouring unit. A single interactive unit, typically the interactive unit on the base of the stack, is attached to a mains power supply and transmits received electric current to the unit which is directly on top of it, and so forth through the stack. This enables the interactive units to be conveniently charged whilst they are arranged in a relatively compact stack and connected to a mains power supply using only a single cable.

The wireless transceivers in the control unit and interactive units comprise circuitry and components capable of supporting wireless communication between the control unit and the interactive unit, for example, Wi-Fi circuitry, Bluetooth circuitry, radio-frequency circuitry, ultrasonic circuitry or infrared circuitry.

The control unit 2 is typically a handheld device made from a lightweight material such as, but not exclusively, a plastics material. For example, the control unit may be a PDA device adapted to carry out remote electronic communication using one or more of wireless communication protocols such as Wi-Fi, Bluetooth, ultrasonic and IR communications wherein the control unit can communicate recorded data to an external user interface, such as a laptop computer, for processing.

In an alternative embodiment, the external user interface may be a personal computer, such as a laptop computer, which also functions as the control unit.

The sporting apparatus is interactive and can react to particular sensing events by providing sensory stimuli responsive to sensing events. The sporting apparatus also records data relevant to a participants performance throughout the game, and relays that data to a control unit which can calculate the data relevant to the performance. The sporting apparatus is adaptable and programmable such that a plurality of games can be played using the apparatus. The control unit can be interfaced with an external network, data source and/or computer to receive program data and upload recorded data relevant to performances.

In use, the control unit distributes programs to each interactive unit each of which stores a program locally. The programs include program code which specifies actions to be carried out when certain events occur (such as sensing events) and data, such as sound data which specifies a sound, for example a spoken instruction. The program may be received through an interface or generated by the control unit.

In use, the stored programs are executed by the microcontroller of each interactive unit. In a preferred embodiment, a computer program is communicated, via the user interface, to the microprocessor of the central control unit.

In turn, the microcontroller in each interactive unit controls the signalling device of that interactive unit according to the program stored in that unit. The actions of the microcontroller, in turn, determine the actions of that interactive unit, causing the signalling device attached to that unit to emit a sensory event, for example to switch on a coloured light. This sensory event is either part of a sequence of different sensory stimuli or it is a single sensory stimulus according to the distributed programs.

In some games, a series of sensory stimuli take place at various interactive units in turn. Individual game participants are issued with an RFID tag 19 selected from a group of RFID tags supplied with the apparatus, each of which includes a unique identifier. Thus game participants can be uniquely identified by the RFID tag reader in the control unit. The or each uniquely identified participant responds to sensory stimuli by navigating to the interactive unit which generates the sensory stimulus.

The or each uniquely identified participant is then required to actuate the button on that interactive unit. Upon the actuation of the button on a particular interactive unit, the microcontroller of that interactive unit stores the response of the uniquely identified participant in the data memory.

If the sensory event is part of a sequence, and it is not the last in a sequence, then another sensory event will be generated by an interactive unit. The distributed program determines which interactive unit emits the new sensory event. If the program requires a different interactive unit to emit a sensory event then the microcontroller of that new interactive unit will be instructed to emit a sensory event by the distributed program stored in its memory device. A new sensory event will then be emitted and the participant must navigate to the new interactive unit and actuate the button on that unit.

Data relating to sensing events is recorded by the data memory in the plurality of interactive units and relayed to the control unit. The relay of data could equally be a continuous communication throughout the game or a single transmission once the game is over. The data relating to sensing events (for example, data communicating that a sensing event has taken place) is relayed from an interactive unit to the control unit and is stored by the control unit.

The microcontroller in the control unit calculates performance data concerning the sensing events which take place at the plurality of interactive units. Typical calculated performance data includes the success or failure of a uniquely identified participant to correctly actuate the button at the correct interactive unit at the correct time or in the correct sequence, the time taken by a uniquely identified participant to navigate their person between interactive units generating sensory stimuli or the total time taken for a uniquely identified participant to correctly recall the sequence in which sensory stimuli were generated by the plurality of interactive units.

The control unit is capable of formatting the calculated data for further processing by a connected external user interface, such as a laptop computer. For example, the formatted data may be converted into a database format file and relayed to a connected laptop for display in a graph or chart. The external user interface may function only to process the formatted data. Alternatively, the external user interface may function to process unformatted data.

The external user interface may function to control the actions of the control unit during a game. Alternatively, the external user interface may function to control the actions of the control unit continuously during a game.

In embodiments which employ the external user interface, such as a laptop computer, which functions as the control unit, data relating to sensing events is recorded by the data memory in the plurality of interactive units and relayed directly to the external user interface. In this case, the external user interface calculates performance data concerning the sensing events which take place at the plurality of interactive units.

Activities which are carried out depend on the programming of the control unit and interactive units. To illustrate the possibilities, several example sporting games are described below.

EXAMPLE GAME 1

In a first example game a program is communicated to the control unit which contains instructions for each of three different interactive units in turn to generate three different sensory stimuli, five seconds apart (the game could equally be played with any number of interactive units, any number of different sensory stimuli generated any time apart). These units are placed remotely from the control unit, each at a distance of 10 m apart (the game could equally be played with the interactive units any distance apart over which wireless electronic communication can operate). There is one participant in this game, Participant A.

The game begins with a button on the control unit being activated by a trainer. In turn, the control unit communicates a program to each interactive unit. The program code contains instructions to generate particular sensory stimuli from particular signalling devices attached to particular interactive units. The program code also contains instructions to communicate to other interactive units and/or to the control unit when a sensing event has occurred.

A first interactive unit then generates a sensory stimulus determined by the program, a coloured red light attached to the unit flashes accordingly. Participant A runs to that unit and presses the button on that unit. Upon pressing the button, the light on that unit stops flashing and a signal is communicated via the transceiver of the first interactive unit to the control unit which indicates a sensing event has occurred. The control unit then communicates to a second interactive unit that the first sensory stimulus has generated a response from Participant A. Equally, the signal may be sent directly to the other interactive units. The time taken for participant A to have responded to the flashing of the coloured red light and actuate the button is recorded by the first interactive unit.

Then, in turn, a second interactive unit is instructed by the control unit to generate a sensory stimulus. Accordingly, a high pitched tone is emitted from the sensory device attached to that unit. Participant A then runs to the second interactive unit and presses the button on that unit. Upon pressing the button on the second interactive unit, the high pitched sound ceases and a signal is communicated via the transceiver to the control unit and/or to the other interactive units that a sensing event has occurred. The second interactive unit records the time taken between participant A pressing the button on the first interactive unit and pressing the button on the second interactive unit.

Finally, the third interactive unit is instructed by the program to generate a sensory stimulus. Accordingly, a spoken audible event is produced; the unit dictates the command "Throw a ball into the basketball net then press the button". Accordingly, Participant A throws a ball into the basketball net then runs to the third unit and presses the attached button. A signal is then communicated to the control unit and/or the other interactive units that the last sensing event in the sequence has occurred. The third interactive unit records the time taken between Participant A pressing the button on the second unit and pressing the button on the third unit. The game is completed upon the actuation of the final button in the sequence.

All three participating interactive units communicate the recorded data to the control unit. The control unit then calculates the total time taken by Participant A to complete the game.

In an alternative embodiment of this game a plurality of participants, Participants A, B, C, D etc. also play. The sequence of sensory stimuli is identical for each participant. The game is played as described above. The time taken for each participant to complete the game is also recorded and compared to the time taken by each other participant to complete the game. In this case, the game is also a contest between participants, with the winner having the shorter total time taken to complete the game. The players could play consecutively. The players could each follow the same route between interactive units, with a delay, and so be participating simultaneously. Performance data relating to each player may be recorded.

EXAMPLE GAME 2

In a second example game, a program is communicated to the control unit containing instructions for one interactive unit to emit a sequence of sensory stimuli at intervals determined by the pressing of the button attached to that unit. There is one participant in this game, Participant A.

The game begins with Participant A activating the control unit. In turn, the control unit communicates the program to the interactive unit. The program code contains instructions to activate particular sensory stimuli in a particular sequence. The program code also contains instructions to communicate to the control unit that a sensing event has occurred whenever a button associated with the interactive unit has been pressed.

The program code also contains instructions to generate the next sensory stimulus in sequence once a sensing event has been sensed. The program code also contains instructions to repeat the sequence of instructions until the sequence of sensory stimuli is complete.

The interactive unit emits the first sensory stimulus accordingly. A spoken audible event is produced; the unit dictates the command "Throw a ball into the basketball net then press the button". Accordingly, Participant A performs the instruction and presses the button. The interactive unit records the time taken between the generation of the sensory stimulus and the actuation of the button.

In turn, the interactive unit emits its second sensory stimulus. A spoken audible event is produced; the unit dictates the command "Run 100 m then press the button". Accordingly, Participant A performs the instruction and presses the button. The interactive unit records the time taken between the generation of the sensory stimulus and the actuation of the button.

This sequence continues until the prescribed number of sensory stimuli has occurred. The interactive unit then communicates the total time taken by Participant A to complete the sequence to the control unit.

In an alternative embodiment of this game a plurality of participants, Participants A, B, C, D etc. also play. There are as many interactive units as participants. The program, containing instructions for one interactive unit to emit a sequence of sensory stimuli at intervals determined by the pressing of the button attached to that unit, is communicated to all participating interactive units. The sequence of sensory stimuli is identical for each participant. The game is played as described above. The time taken for each participant to complete the game is also recorded and compared to the time taken by each other participant to complete the game. In this case, the game is also a contest between participants, with the winner having the shorter total time taken to complete the game.

EXAMPLE GAME 3

In a third example game, a program is communicated to the control unit containing instructions for the plurality of interactive units to emit a sequence of sensory stimuli at intervals of 2 seconds, each for a duration of 2 seconds (the interval and duration concerning any sensory stimulus may be of any arbitrary length appropriate to the game). Each interactive unit is identifiable by a distinct numbered label. There is one participant in this game, Participant A.

The game begins with Participant A activating the control unit. In turn, the control unit communicates the program to the plurality of interactive units. The program code contains instructions to activate particular sensory stimuli in a particular sequence at particular interactive units. The game begins.

The first interactive unit activates a red light. After 2 seconds the light goes out and 2 seconds later a different interactive unit illuminates with a red light. After 2 more seconds that light goes out and is followed by a sequence of illuminations on different interactive units, each lasting for 2 seconds and occurring 2 seconds apart. After a length of time, predetermined by the program, the sequence ends. Participant A now recalls the sequence in which the interactive units were illuminated and runs to each interactive unit in turn, according to the sequence of sensory events, and actuates the sensor on each interactive unit, repeating the order of the sequence.

The control unit records the success or failure of Participant A to correctly recall the sequence of illumination.

In a variation of this game, if Participant A correctly recalls the sequence of illumination then another sequence of greater length begins.

In a further variation of this game, different colours of light may be emitted by different interactive units at different points throughout the sequence and Participant A must correctly recall both the order of illumination and the colour of each illumination.

Various other games can be played and are subject to the program communicated to the control unit.

In a second embodiment of the present invention, the function of the program is replaced by a manual operation. The input device, for example a keyboard, on the control unit has a plurality of keys each relating to the plurality of interactive units. When a particular key is pressed on the control unit the signalling device on the interactive unit corresponding to that key is activated. A participant of the game responds in the same manner described above. Data relating to the sensing events is recorded, distributed and calculated in the manner corresponding to the previous embodiment.

In a further embodiment of the present invention, there is provided an identifying unit comprising a unique identifying tag reader capable of reading and identifying unique RFID tags. A game participant is issued with a unique RFID tag which is carried during participation of a game. When a game participant is proximate to the identifying unit the unique identifying tag reader of said unit identifies the individual game participant proximate to the identifying unit and communicates that information to the control unit. The control unit records data relating to that particular game participant accordingly.

In games where there is a plurality of participants taking part simultaneously, each game participant is issued with a unique RFID tag. The unique identifying tag reader uniquely identifies each game participant and communicates that information to the control unit. The control unit records data relating to each individual game participant accordingly.

Figure 3:
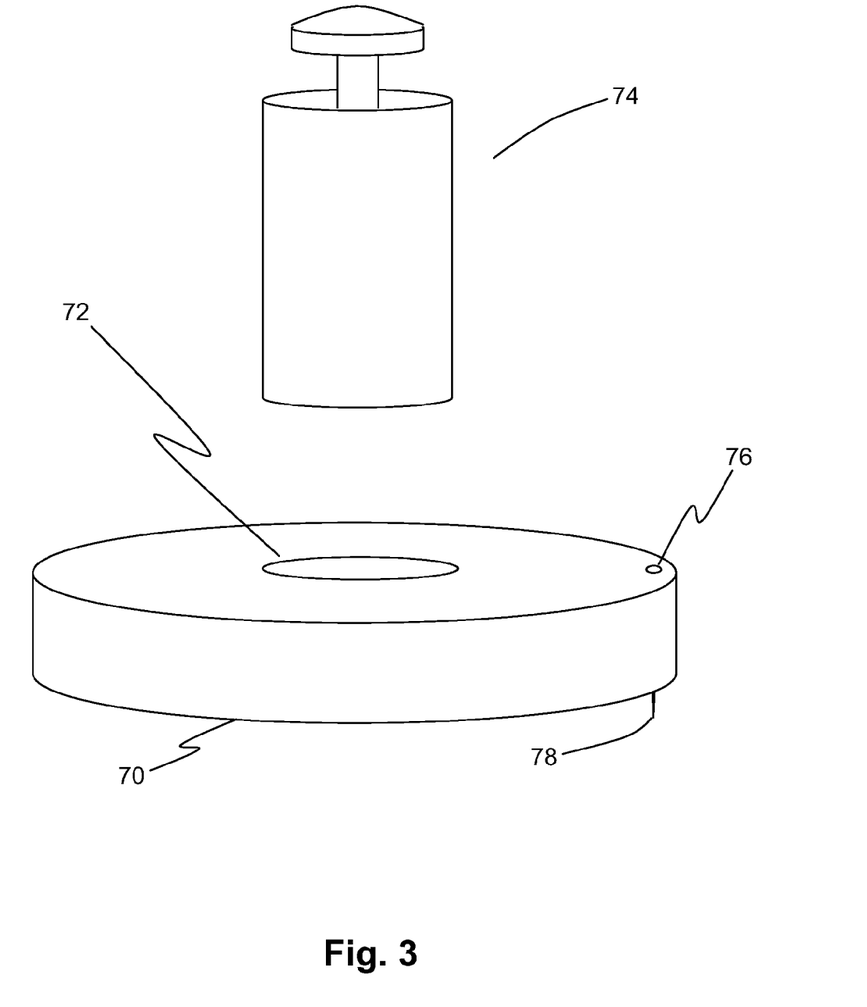
FIG. 3 is a perspective view of a remote unit in another embodiment of the interactive sporting apparatus.

An embodiment of a remote unit 70 is shown in FIG. 3. The remote unit comprises an interface 72 capable of demountably retaining a signalling device 74 selected from a plurality of signalling devices. Equally, the interface can demountably retain a sensor. The remote unit further comprises electronic contacts comprising a socket 76 and a plug 78 which are arranged, so that when the remote units are stacked upon each other, the electronic contacts of successive units within the stack are operable to transfer electric current to a neighbouring unit.

In use, each remote unit can be customised to a produce a particular sensory stimulus by attaching a particular signalling device via the interface to the remote unit. Equally, the remote units can be customised with a particular sensor attachment.

In use, the interactive sporting apparatus comprises a plurality of remote units which can communicate with the control unit in the manner described for the embodiment employing interactive units.

The remote units can be customised, and as such, they provide new advantages over the embodiments which employ the interactive units of the first aspect of the invention. The interactive sporting apparatus may comprise remote units such that all the remote units comprise an attached sensor, such as a proximity sensor. The proximity sensor is operable by a game participant proximate to that remote unit. In this case, the interactive sporting apparatus records data relating to participants or teams of participants participating in a sporting game such as a team race between remotely placed remote units.

Alternatively, the interactive sporting apparatus may comprise remote units such that all the remote units comprise an attached signaling device, such as a coloured light or loudspeaker. In this case, the interactive sporting apparatus records data relating to a sequence of sensory stimuli such as the sequence described in a memory game such as Example Game 3. A game participant would enter the recalled sequence into the control unit or an external user interface.

Alternatively, the plurality of remote units could each comprise either an attached signaling device or an attached sensor. In this case, the interactive sporting apparatus may be operable to record data relating to a game requiring a participant to respond to both sensory stimuli and to generate sensing events, for example a participant may be required to run to a remote unit generating a sensory stimulus such as a coloured light, and then throw a bean bag to hit another remote unit comprising a proximity sensor to generate a sensing event.

In another embodiment, the interactive sporting apparatus could comprise remote units, wherein at least one of the remote units comprises an interface adapted to demountably retain an exchangeable device comprising both a signaling device and a sensor selected from a plurality of different exchangeable devices. In this case, the interactive sporting apparatus can be customised for the needs of particular users or groups of users by attaching different exchangeable devices with particular combinations of signaling devices and sensors to particular remote units.

In yet another embodiment, the interactive sporting apparatus could comprise remote units, wherein at least one of the remote units comprises an interface adapted to demountably retain either a signaling device or a sensor, or to demountably retain an exchangeable device comprising both a signaling device and a sensor. In this case, an assembled remote unit would comprise either a demountably retained signaling device selected from a plurality of different signaling devices, or a demountably retained sensor selected from a plurality of sensors, or a demountably retained exchangeable device comprising both a signaling device and a sensor selected from a plurality of exchangeable devices.

In this case, the interactive sporting apparatus can be further customised for the needs of a particular user. For example, some assembled remote units may comprise a sensor only, other remote units may comprise a signaling device only, and the remaining remote units may comprise an exchangeable device comprising both a signaling device and a sensor.

In a further embodiment, each remote unit interfaces with an exchangeable device comprising both a signaling device and a sensor.

Further modifications and variations may be made by one skilled in the art within the scope of the invention herein disclosed.

The invention claimed is:

1. Interactive sporting apparatus comprising a control unit and a plurality of remote units, the remote units comprising a ground engaging base having either:
   (i) an interface for demountably retaining: (a) a signalling device for generating a sensory stimulus; or (b) a sensor operable by a game participant proximate to the remote unit, for generating a sensing event, or
   (ii) an interface for demountably retaining a device which comprises both a signalling device for generating a sensory stimulus and a sensor operable by a game participant proximate to the remote unit, for generating a sensing event, and a plurality of exchangeable sensors of different types which are demountably attachable to the interface of a remote unit, at least one of the sensors being remotely actuated, wherein the control unit is operable to communicate remotely with the plurality of remote units to specify sensory stimuli to be generated by one or more remote units.

2. Interactive sporting apparatus according to claim 1, wherein the interface of a remote unit is adapted to demountably retain a signalling device or a sensor, or a device which comprises both a signalling device and a sensor.

3. Interactive sporting apparatus according to claim 1, wherein the apparatus comprises a plurality of different exchangeable devices comprising both a signalling device and a sensor which are demountably attachable to the interface of a remote unit.

4. Interactive sporting apparatus according to claim 3, wherein at least one exchangeable device comprises a sensor, wherein the sensor is remotely operable.

5. Interactive sporting apparatus according to claim 1, wherein the control unit is adapted to communicate with and receive instructions from or communicate stored performance data to an external computer.

6. Interactive sporting apparatus according to claim 1, wherein each remote unit comprises a programmable electronic controller which is operable to control the generation of sensory stimuli by the signaling device dependent on a program.

7. Interactive sporting apparatus according to claim 1, wherein the apparatus comprises a plurality of exchangeable signaling devices of different types which are demountably attachable to the interface of a remote unit.

8. Interactive sporting apparatus according to claim 1, wherein the apparatus is operable to record data relating to sensing events.

9. Interactive sporting apparatus according to claim 8, wherein the control unit is operable to record performance data relating to one or more participants in a sporting game using the interactive sporting apparatus simultaneously or consecutively.

10. Interactive sporting apparatus according to claim 1, wherein the control unit is adapted to communicate with and receive instructions from an external computer.

11. Interactive sporting apparatus according to claim 1, wherein the control unit is adapted to communicate stored performance data to an external computer.

12. Interactive sporting apparatus according to claim 1, wherein the control unit and the plurality of remote units are operable to form a wireless communications network.

13. Interactive sporting apparatus according to claim 1, wherein two or more of the plurality of remote units interact differently with participants.

14. Interactive sporting apparatus according to claim 1, wherein two or more of the remote units are labeled differently.

15. Interactive sporting apparatus according to claim 1, wherein the remote units comprise internal power supplies.

16. Interactive sporting apparatus according to claim 1 comprising a unique identifying tag reader.

17. Interactive sporting apparatus according to claim 16 comprising a plurality of unique identifying tags.

18. Interactive sporting apparatus according to claim 1, wherein the interface of a remote unit is adapted to demountably retain a signalling device or a sensor, but not a device which comprises both a signalling device and a sensor.

19. Interactive sporting apparatus according to claim 1 wherein the interface of a remote unit is adapted to demountably retain a device which comprises both a signalling device and a sensor.

20. Interactive sporting apparatus according to claim 1 further comprising a plurality of signalling devices each of which is demountably attachable to the interface of a remote unit.

21. Interactive sporting apparatus according to claim 1 wherein the remote units can be placed remotely from each other in use.

22. Interactive sporting apparatus according to claim 1 wherein the remote units can be placed remotely from the control unit in use.

23. A method of using interactive sporting apparatus comprising a control unit and a plurality of remote units, the remote units comprising a ground engaging base having either:
  (i) an interface for demountably retaining a signalling device for generating a sensory stimulus or a sensor operable by a game participant proximate to the remote unit, for generating a sensing event, or
  (ii) an interface for demountably retaining a device which comprises both a signalling device for generating a sensory stimulus and a sensor operable by a game participant proximate to the remote unit, for generating a sensing event, and
  a plurality of exchangeable sensors of different types which are demountably attachable to the interface of a remote unit, at least one of the sensors being remotely actuated,
  wherein the control unit is operable to communicate remotely with the plurality of remote units to specify sensory stimuli to be generated by one or more remote units,
  the method comprising customising one or more of the said remote units by demountably attaching a respective exchangeable sensor from the said plurality of exchangeable sensors to each of the said one or more remote units via their respective interfaces.

24. The method according to claim 23 further comprising placing the remote units remotely from each other.

25. The method according to claim 23 further comprising placing the remote units remotely from the control unit.

26. The method according to claim 23 wherein the interactive sporting apparatus further comprises a plurality of signaling devices each of which is demountably attachable to the interface of a remote unit, the method further comprising customizing one or more remote units by demountably attaching a respective signaling device from the said plurality of signaling devices to each of the said one or more remote units via their respective interfaces.

* * * * *

UNITED STATES PATENT AND TRADEMARK OFFICE
CERTIFICATE OF CORRECTION

PATENT NO. : 8,771,073 B2  
APPLICATION NO. : 13/060145  
DATED : July 8, 2014  
INVENTOR(S) : Klinnert et al.

Page 1 of 1

It is certified that error appears in the above-identified patent and that said Letters Patent is hereby corrected as shown below:

On the Title Page

Item (12) should read: -- (12) Klinnert et al. --

Item (75) Inventors should read:

-- (75) Inventors:

Ralf Klinnert, Edinburgh (UK); and

Thomas David Binnie, Edinburgh (UK) --

Signed and Sealed this  
Tenth Day of February, 2015

Michelle K. Lee  
*Deputy Director of the United States Patent and Trademark Office*